US00PP21431P3

(12) United States Plant Patent
Sonnoli et al.

(10) Patent No.: US PP21,431 P3
(45) Date of Patent: Nov. 2, 2010

(54) 'VAS-ONE' OLIVE TREE

(50) Latin Name: *Olea europaea*
Varietal Denomination: Vas-One

(75) Inventors: Elena Sonnoli, Pescia (IT); Alberto Sonnoli, Montecatini Terme (IT); Stefano Sonnoli, Pescia (IT)

(73) Assignee: Vivai Attilio Sonnoli Societa Agricola Semplice

( * ) Notice: Subject to any disclaimer, the term of this patent is extended or adjusted under 35 U.S.C. 154(b) by 0 days.

(21) Appl. No.: 12/378,611

(22) Filed: Feb. 17, 2009

(65) Prior Publication Data

US 2009/0255017 P1 Oct. 8, 2009

(30) Foreign Application Priority Data

Apr. 4, 2008 (IT) ..... 2008/0715

(51) Int. Cl.
*A01H 5/00* (2006.01)

(52) U.S. Cl. ..... Plt./158

(58) Field of Classification Search ..... Plt./158
See application file for complete search history.

(56) References Cited

U.S. PATENT DOCUMENTS

| | | | |
|---|---|---|---|
| PP5,829 | P | 12/1986 | Haas |
| PP7,750 | P | 12/1991 | Zampini |
| PP10,641 | P | 10/1998 | Sonnoli, Jr. |
| PP13,077 | P2 | 10/2002 | Fontanazza |
| PP18,598 | P3 | 3/2008 | Tous |
| PP18,599 | P3 | 3/2008 | Tous |
| PP18,600 | P3 | 3/2008 | Tous |

OTHER PUBLICATIONS

Tous, et al. "IRTA-i-18": A Clone of the "Arbequina" Olive Variety, Olivae, No. 77, Jun. 1999, pp. 50-52.
California Olive Oil News, vol. 5, Issue 7, Jul. 2002 (online, retrieved on Dec. 5, 2005). Retrieved from the internet <http://www.oliveoilsource.com/newsletter/olivenews5-7.htm> pp. 1-10.
IRTA, The Arbequina Irta-i-18 Olive Clone (online, retrieved on Apr. 18, 2006). Retrieved from the internet <http://www.irta.es.eng/index.html>, 5 pages.
Garden Web Glossary of Botanical Terms (online, retrieved on Dec. 20, 2006). Retrieved from the internet <http://glossary.gardenweb.com/glossary/> 3 pages.
The New Royal Horticultural Society Dictionary of Gardening, 1992, vol. 3, p. 354.
California Olive Oil News, vol. 6, Issue 12, Dec. 2003 (online, retrieved on Apr. 18, 2006). Retrieved from the internet <http://www.oliveoilsource.com/newsletter/olivenews6-12.htm> 10 pages.
Garden Web Glossary of Botanical Terms (online, retrieved on Jan. 8, 2007). Retrieved from the internet <http://glossary.gardenweb.com/glossary/> 3 pages.
Tous et al. Arbosana Irta-i-43, Catalonia Agroinifora Journal, No. 2, Aug. 2000 pp. 13, 15.
IRTA (online, retrieved on Apr. 8, 2006). Retrieved from the internet <http://www.irta.es.eng/index.html>, 4 pages.

*Primary Examiner*—June Hwu
(74) *Attorney, Agent, or Firm*—Mark D. Miller

(57) ABSTRACT

The present selection comprises a new and distinct seedling system of *Olea europaea*. This new invention appears to be resistant to pests, diseases and cold temperatures while producing an excellent olive fruit within six to eight years and is primarily grown for olive oil production. The fruit matures in the Tuscany area of Italy in late October to mid-November.

7 Drawing Sheets

BACKGROUND OF THE NEW VARIETY

The present invention relates to a new and distinct variety of olive plant, *Olea europaea*, and will hereinafter be denominated varietally as 'VAS-ONE' and more particularly to an olive plant that produces fruit for harvest between late October and mid-November in the Tuscany area of Italy and which is further distinguished by having heavy production and very good oil yield: 60-80% more than the minimum oil of 12% within 6 years, as well as resistance to low temperature. The mother tree is eighteen years old and was discovered in the Uzzand via Darrath-Pistaqa area, Italy with the following dimensions: height 8.2 feet (250 cm) and width 9.84 feet (300 cm). Seedlings were collected from around the mother tree.

This new invention relates to a new and distinct variety of olive tree from a seedling; was selected from a group of seedlings collected from around a mother tree in an olive orchard after 10 years of observation; vegetatively propagated in 2008 and exported to the United States. The cultivar names of the parent trees are not known. This new variety, 'VAS-ONE' has superior production with superior oil quality and prediction.

ORIGIN AND ASEXUAL PRODUCTION

The new variety has been asexually propagated in an olive orchard north of Tuscany, Italy by way of vegetative propagation by rooted cuttings. The new variety is distinguished from its parents in that it produces high oil yields and is somewhat resistant to pests and diseases, and to low temperature and it has very good vigor and high productivity. The plant is suited for olive oil production with the fruit maturing late October to mid-November.

At the site north of Tuscany, after verification of the superior characteristics in production uniformity, olive oil production and quality, vegetatively reproduced cuttings were sent to the U.S.A. in 2008. Upon completion of the post-entry quarantine requirements in California, additional cuttings will be asexually propagated.

SUMMARY OF THE NEW VARIETY

The new variety of olive was discovered through a selection process from an olive orchard in Tuscany, Italy. Through a selection process beginning in 1998 over a ten year period, the seedling selection process was completed. The new variety is late maturing from late October to mid-November with high productivity and good oil yield within 6-8 years.

DETAILED DESCRIPTION

Figure 1:
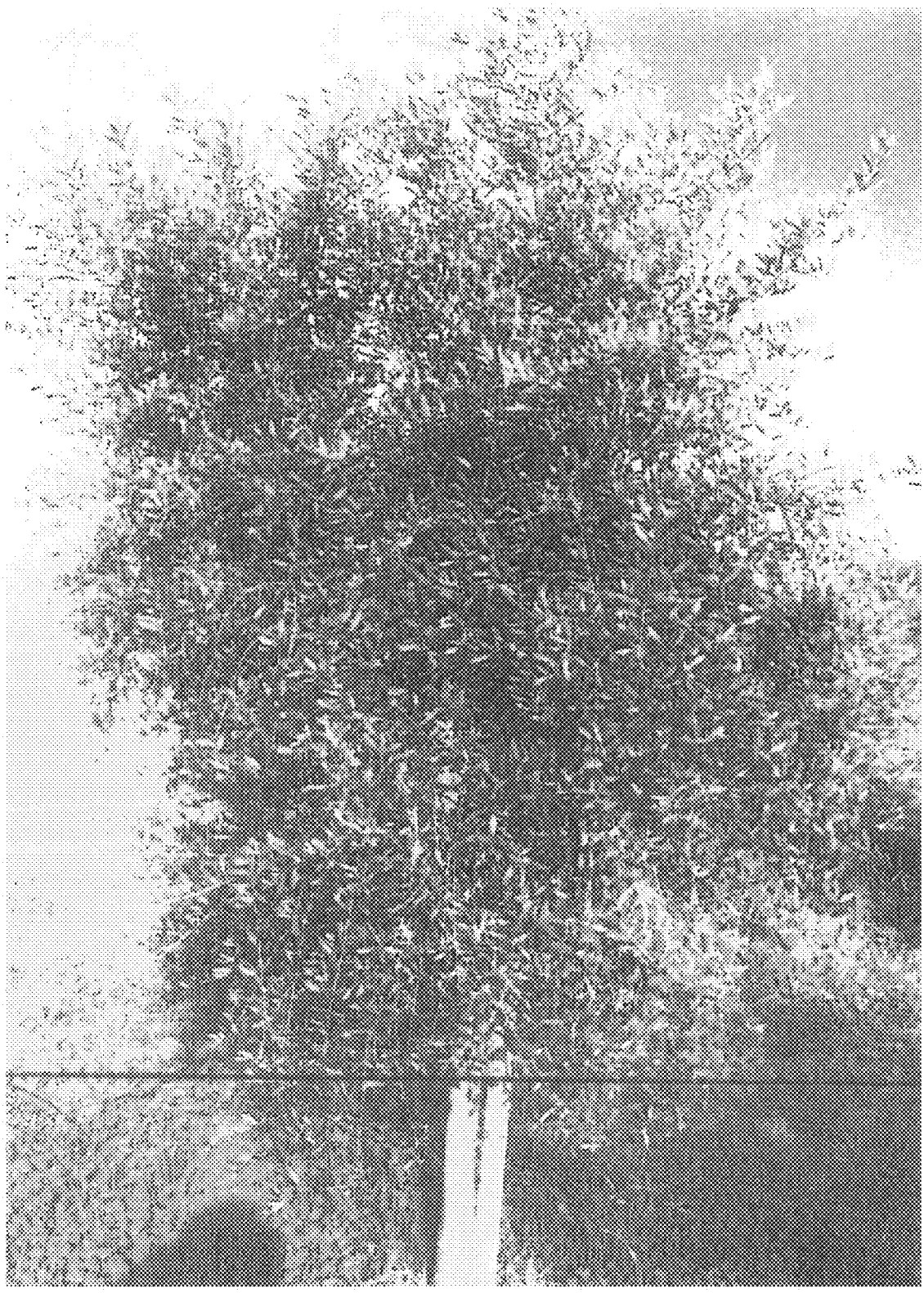
FIG. 1 displays a view of the new variety tree.
Figure 2:
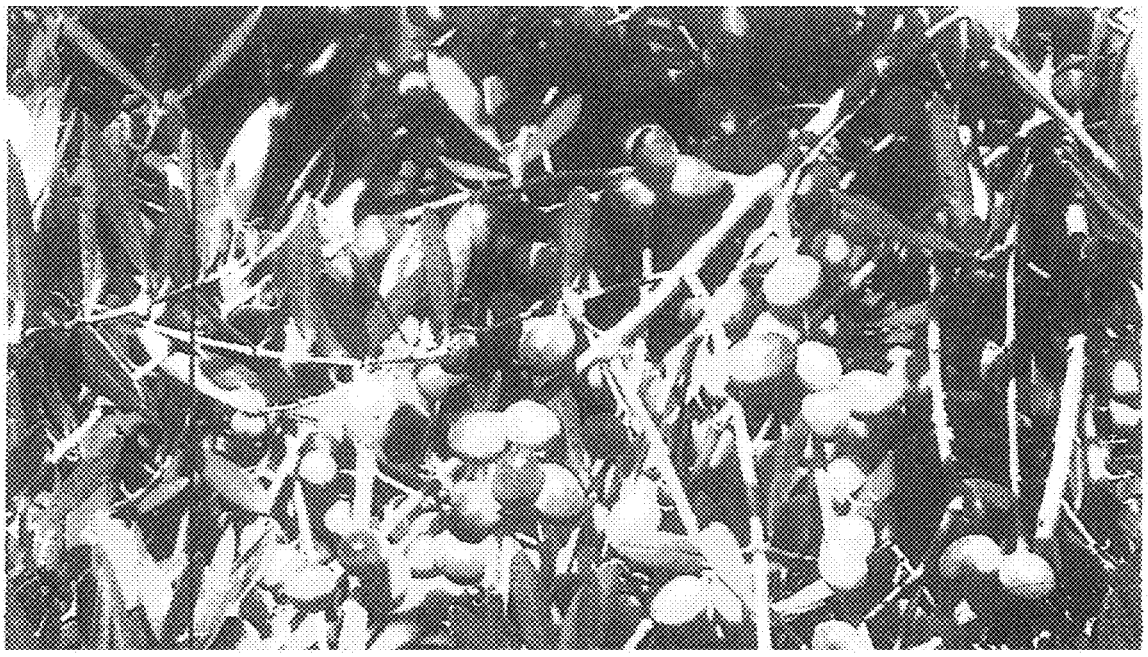
FIG. 2 displays the fruit and fruit clusters along with leaves and young branches.
Figure 3:
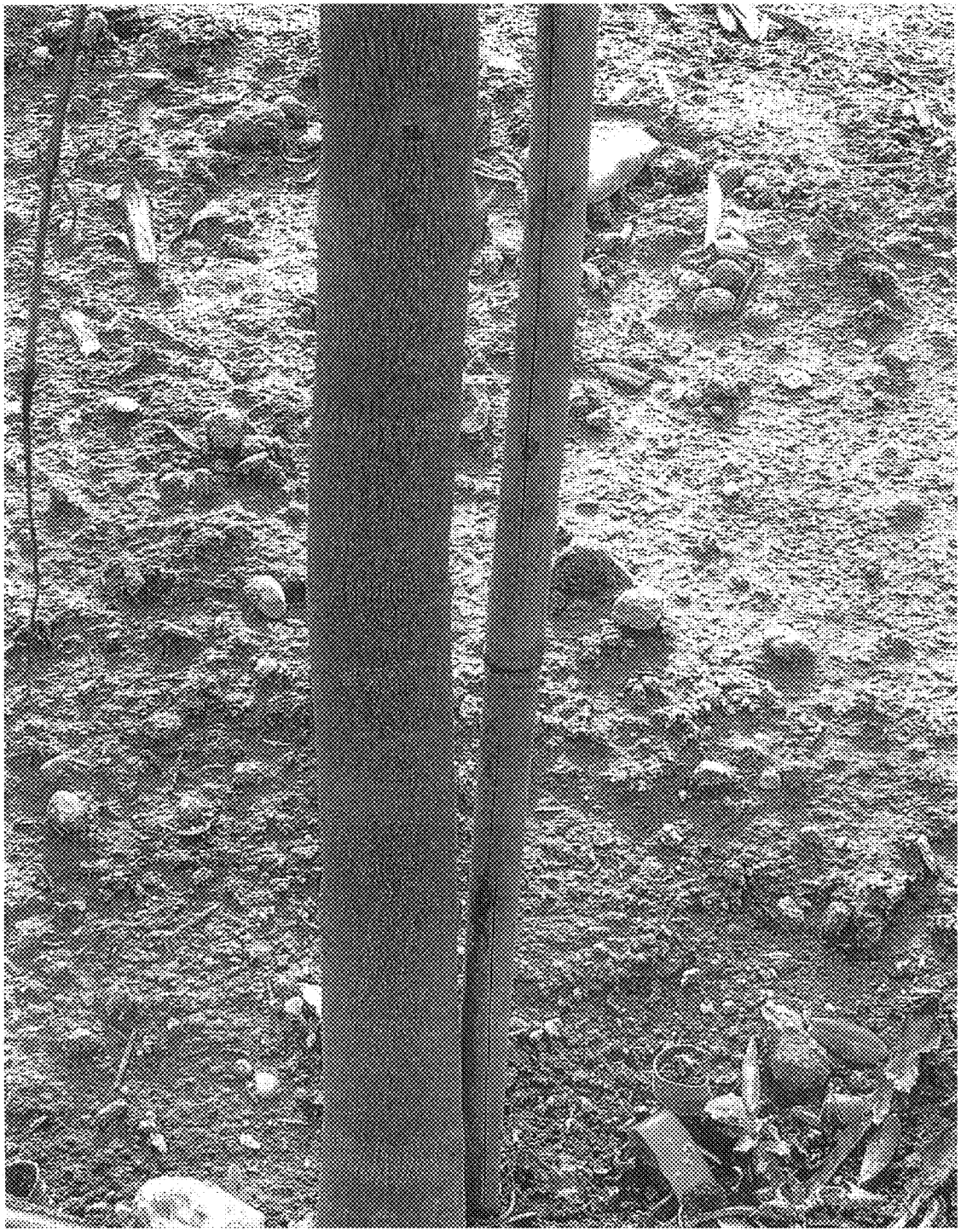
FIG. 3 displays of the mature trunk of the new variety.
Figure 4:
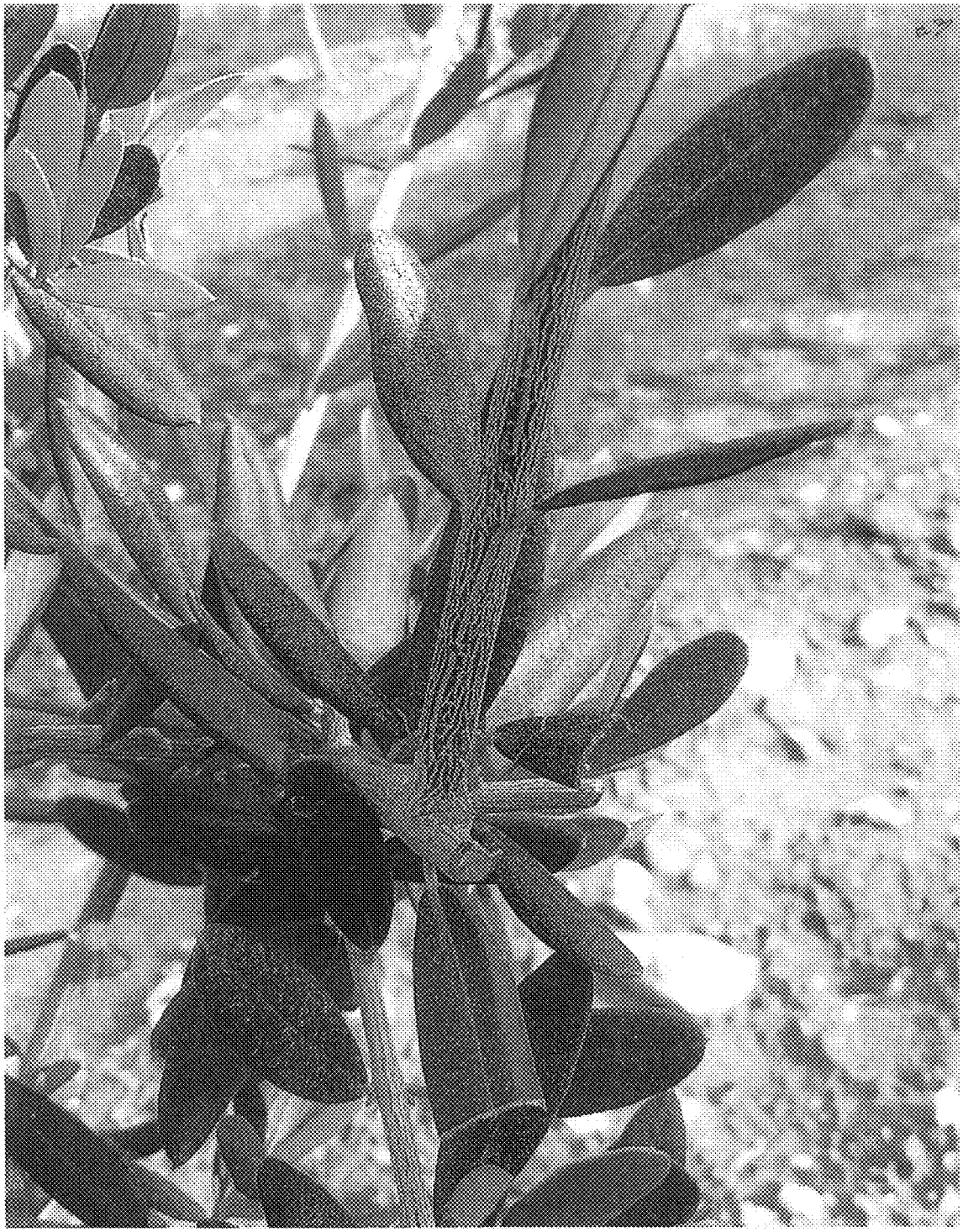
FIG. 4 displays of the two year or older branches with leaves.
Figure 5:
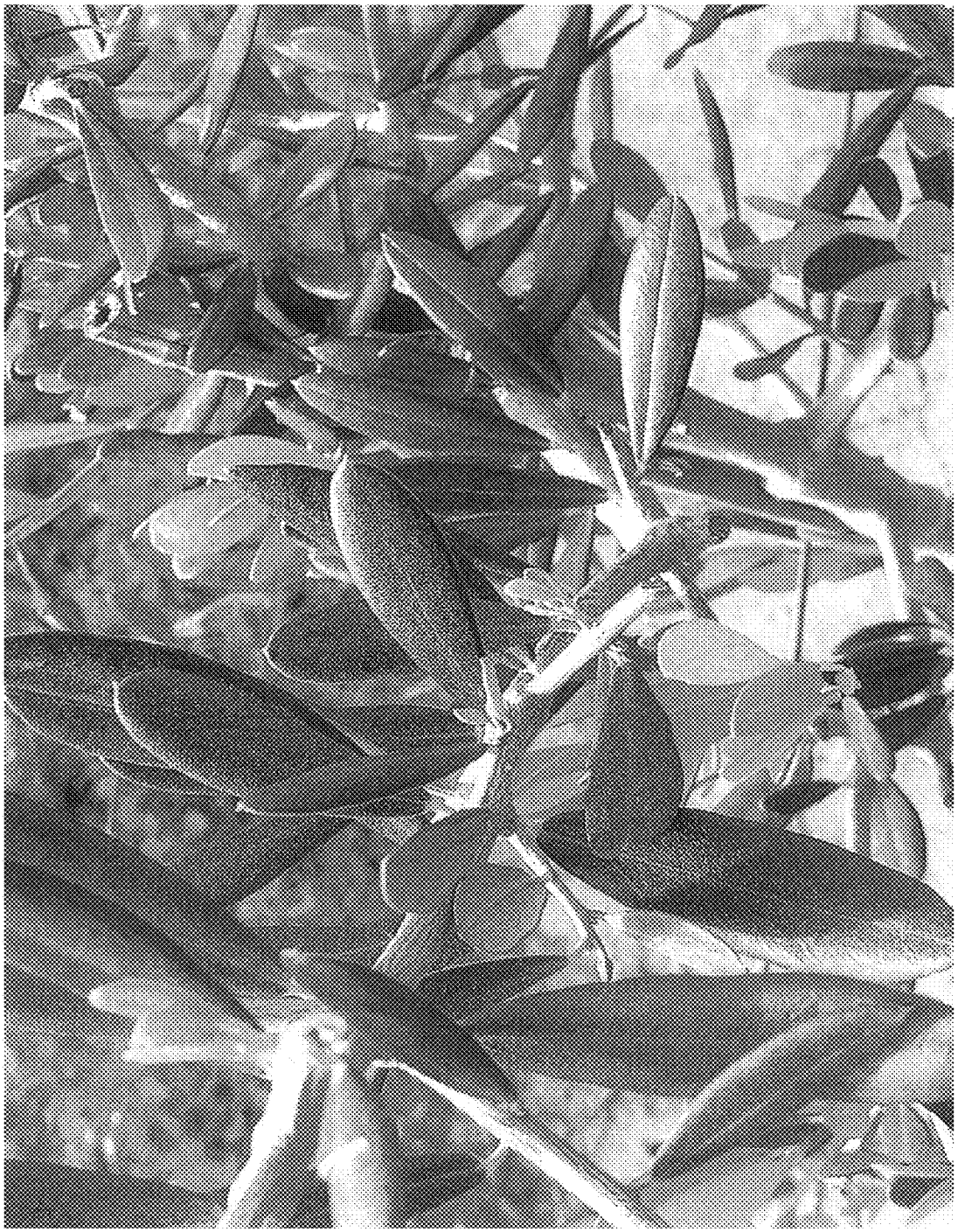
FIG. 5 displays younger branches 1 year old along with older ones.
Figure 6:
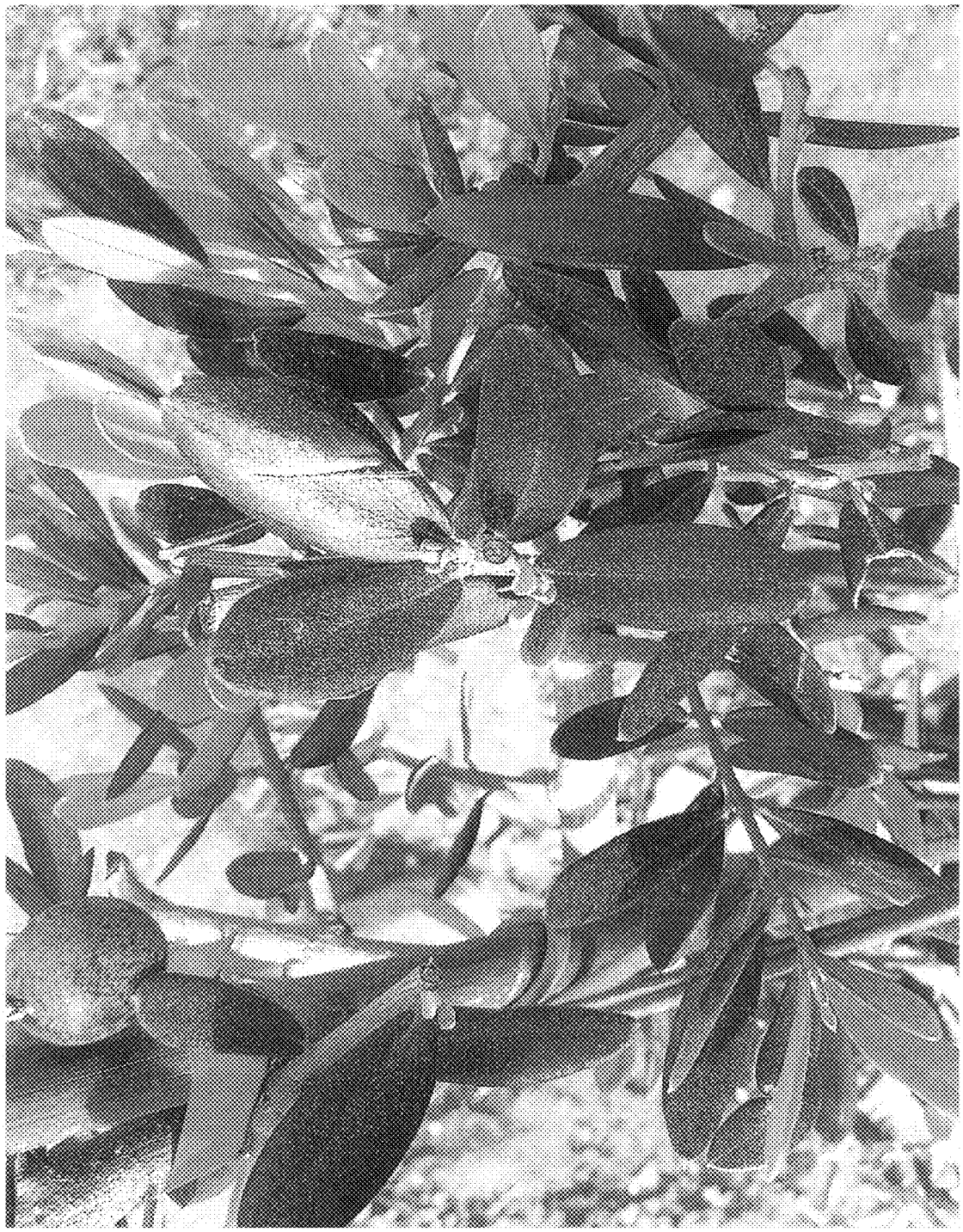
FIG. 6 displays leaves with a mature fruit.
Figure 7:
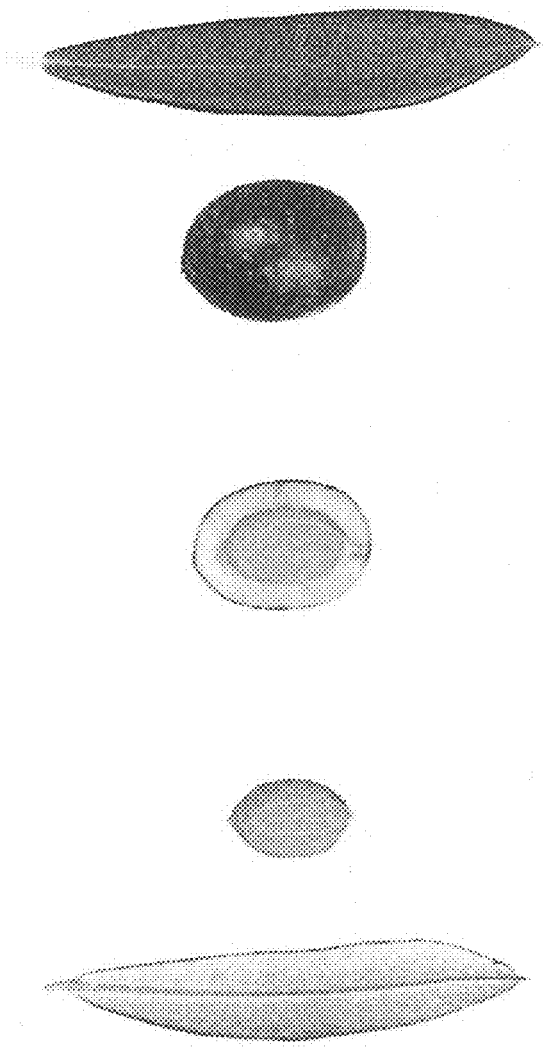
FIG. 7 displays upper leaf and lower leaf surfaces, mature fruit, fruit cut half with seed, and seed.

Referring more to the horticultural description and details of the new and distinct variety of olive tree, the following description has been observed under the ecological conditions prevailing in Tuscany, Italy. The age of the observed plant was 6-8 years. All major color designations are by reference to the Dictionary of Color by Maerz & Paul, First Edition, 1930. Common colors are also employed.

Tree

This new invention has medium size trees.

Height: 8.2 ft. (250 cm)

Width: 9.84 ft. (300 cm)

Vigor: Good

Chilling requirements: Normal for olive trees in the Sacramento Valley

Figure: Upright and somewhat pyramidal

Productivity: Very good

Regularity of bearing: Alternate

Trunk

Size: 11.8 ft. (36 cm)

Circumference: 36 cm (measurement taken about 12 inches above ground)

Surface texture: Smooth

Color code: Dutch Bl. (44-A-6)

Branches:

*Mature* (1 *year or older*).—Circumference: 0.26 inch (6.5 mm).

*Immature* (*less than* 1 *year*).—Circumference: 0.20 inch (5.0 mm).

*Surface texture.*—Mature: smooth. Immature: smooth.

*Color.*—Mature: Light Wedgwood (37-A-7) is the basic color with Slate (39-A-7) as the darker streaked top. Immature: Opaline Gr. (17-A-6).

*Lenticels.*—None.

Leaves

Size: Small, opposite

Length: Average 1.87 inch (47.4 mm)

Width: Average 0.49 inch (12.4 mm)

Shape: Elliptical

Margin: Entire

Apex: Obtuse

Base: Cuneate

Surface texture:

*Upper surface.*—Smooth.

*Downward surface.*—Slightly pubescent.

Color:

*Upward.*—Polo Green (23-J-9).

*Downward.*—Mignon Green (21-J-6).

Leaf vein:

*Color.*—Mignon Green (21-J-6).

*Thickness.*—1 mm (0.04 in).

Granular characteristics: None

Petiole: Short, 4-5 mm (0.16-0.20 inch)

*Thickness.*—1-1.5 mm (0.04-0.06 inch).

*Color.*—Parrot Green (21-L-6).

Thickness.—2 mm (0.08 inch)

Stem glands: None

Flower

Flower buds: Small, slightly pubescent

Average. bud size: Small, 2-4 mm (0.08-0.16 inch)

Date of first bloom: Mid-May

*Size.*—Small.

*Petals.*—4.

Number of florets per inflorescence: 10-16

Inflorescence: Average length of 3 to 4 inches (7.62-10.16 cm)

Inflorescence type: Raceme

Number of sepals: 4

Number of petals: 4

*Color.*—White (1-A-1).

Fragrance: Very mild

Reproductive organs: 1 Pistil; 16-27 stamens

Pollen color: Empire Yellow (9-K-3)

Fruit

Date of maturity: Late October to mid-November

Size: Small

Weight: 1.85 grams

Diameter: 12-14 mm (0.47-0.55 inch)

Length: 14-20 mm (0.55-0.79 inch)

Form: Ovate

Suture: None

Stem cavity:

*Width.*—7 mm (0.28 inch).

*Depth.*—Average 7 mm (0.28 inch).

*Length.*—7 mm (0.28 inch).

Stem: Average 4.8 mm (0.19 inch)

*Caliper.*—Very small.

Pistil point: Obscure

Fruit flesh color: Pinnard Yellow (9-J-2)

Fruit surface color: Dark brown, Annapolis (40-C-6)

Color of pit: Pinnard Yellow (9-J-2).

Skin

Thickness: Less than 1 mm (less than 0.04 inch)
Texture: Smooth
Tendency to crack: None Seed Type: Cling
Fibers: None
Size:
*Length.*—Approximately 14 mm (0.55 inches).
*Width.*—Approximately 9 mm (0.35 inches).
*Thickness.*—Approximately 9 mm (0.35 inches).
Form: Elliptical
Apex: Slightly pointed
Color: Blush Peach Beige (11-A-6)
Base: Slightly truncate
Mucron: Obscure
Suture: Slightly marked
Sides: About even
Ridges: Faint and uneven
Tendency to split: None known
Use: Oil production
Resistance: Yes, to pests and diseases such as Peacock spot (*Spilocaea oleaginea*)
Harvesting: Mechanical Oil Virgin oil fatty acid percentages:
*Miristic acid.*—0.005%.
*Palmitic acid.*—13.112%.
*Palmitoleic acid.*—0.795%.
*Margaric acid.*—0.044%.
*Margaroleic acid.*—0.078%.
*Estearic acid.*—2.465%.
*Oleic acid.*—72.909%.
*Linoleic acid.*—9.034%.
*Araquidic acid.*—0.361%.
*Linolenic acid.*—0.829%.
*Gadoleic acid.*—0.238%.
*Behenic acid.*—0.099%.
*Lignoceric acid.*—0.026%.
M/P ratio (monosaturated fats/polysaturated fats): 5.4
Polyphenols (ppm caiteic acid): 400 ppm (mg/Kg)
K225 (bitterness): 1

What is claimed is:

1. A new distinct olive plant as described above with better vigor and higher productivity than 'Minerva' with very good fruit production for olive oil within six to eight years with fruit maturing in late October to mid-November in the Tuscany area of Italy.

* * * * *